United States Patent [19]

Speranza et al.

[11] Patent Number: 5,095,116
[45] Date of Patent: Mar. 10, 1992

[54] BLOCK AMIDO-AMINE CONDENSATION PRODUCTS

[75] Inventors: George P. Speranza, Austin; Jiang-Jen Lin, Houston, both of Tex.

[73] Assignee: Texaco Chemical Company, White Plains, N.Y.

[21] Appl. No.: 576,825

[22] Filed: Sep. 4, 1990

[51] Int. Cl.$^5$ .......................................... C07D 241/04
[52] U.S. Cl. ............................... 544/400; 528/118; 528/73
[58] Field of Search .................................... 544/400

[56] References Cited

U.S. PATENT DOCUMENTS

| | | | |
|---|---|---|---|
| 3,257,342 | 6/1966 | Kwong | 260/18 |
| 3,654,370 | 4/1972 | Yeakey | 260/584 |
| 4,062,819 | 12/1977 | Mains et al. | 260/18 |
| 4,062,820 | 12/1977 | Mitchell et al. | 260/18 |
| 4,119,615 | 10/1978 | Schulze | 528/343 |
| 4,133,803 | 1/1979 | Klein | 528/340 |
| 4,218,351 | 8/1980 | Rasmussen | 260/18 |
| 4,239,635 | 12/1980 | Rieder | 252/34 |
| 4,588,783 | 5/1986 | Chang | 525/329.9 |
| 4,751,255 | 6/1988 | Bentley et al. | 521/163 |

*Primary Examiner*—C. Warren Ivy
*Assistant Examiner*—James H. Turnipseed
*Attorney, Agent, or Firm*—Jack H. Park; Kenneth R. Priem; Carl G. Ries

[57] ABSTRACT

A block amido-amine condensation product having the formula:

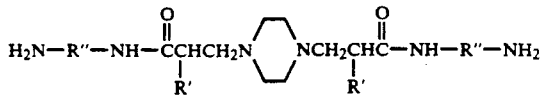

wherein
R' represents hydrogen or methyl, and
R'' represents an organic group selected from the group consisting of polyoxyethylene groups, polyoxypropylene groups, polyoxyethylene/oxypropylene groups, and polyethylene amino groups.

7 Claims, No Drawings

BLOCK AMIDO-AMINE CONDENSATION PRODUCTS

BACKGROUND OF THE INVENTION

1. Technical Field of the Invention

This invention relates to block amido-amine condensation products. More particularly, this invention relates to water-soluble block amido-amine condensation products derived from piperazine; an unsaturated acid component, which may be acrylic or methacrylic acid or a $C_1$–$C_8$ alkyl ester thereof, and an organic di-primary amine component, which may be a polyoxyethylene diamine, a polyoxypropylene diamine, a polyoxyethylene/oxypropylene diamine or a polyethylenepolyamine, all as herein defined. Still more particularly, this invention relates to block amido-amine condensation products prepared by reacting piperazine with an unsaturated acid component in the ratio of about 2 moles of unsaturated component per mole of piperazine to provide an intermediate reaction product which is then reacted with an organic diprimary amine component in the ratio of about 2 moles of diprimary amine component per mole of piperazine in order to provide the block amido-amine condensation products as the principle products of the reaction. The reactions, which do not require the use of a catalyst, are preferably conducted at a temperature of about 150° to about 250° C. and a pressure of about 0 to 500 psig.

The block amido amine condensation products of the present invention can be used as raw materials for a wide variety of purposes such as, for example, as chain extenders for epoxy resins, curing agents for epoxy resins, as raw materials for the manufacture of polyureas, thickening agents, etc. The products may also be used as raw materials for the preparation of fuel and lubricant additives, for textile and fiber treating agents, for the preparation of adhesives, for use in the manufacture of polyureas, for use in encapsulation and molding applications, etc.

2. Prior Art

It is known, as exemplified by Yeakey U.S. Pat. No. 3,654,370 to prepare polyoxyalkylene polyamines by the reductive amination of a polyoxyalkylene polyol. The reductive amination is conducted catalytically in the presence of hydrogen and ammonia and an appropriate reductive amination catalyst, such as a nickel, copper and chromia catalyst. The polyoxyalkylene polyamines that are prepared in this fashion are stable articles of commerce having a wide variety of uses such as those mentioned above. In particular, they have found utility as curing agents for epoxy resins, as plasticizers, as cross linking agents and binders for textiles, and as intermediates in the preparation of polyureas. In general, polyoxyalkylene polyamines having molecular weights ranging from about 200 to about 5,000 can be prepared by the Yeakey process.

Kwang U.S. Pat. No. 3,257,342 is directed to epoxy resins that are cured with a polyamidodiamine prepared by reacting about two molar equivalents of a polyoxyalkylenediamine with an aliphatic dicarboxylic acid.

Klein U.S. Pat. No. 4,133,803 is directed to the preparation of novel thermoplastic adhesive compositions having melting points between 20° and 180° C. prepared by reacting a polyoxypropylene diamine or triamine with an aliphatic or aromatic dicarboxylic acid, ester or anhydride thereof. In his working examples, Klein used approximately equimolar amounts of carboxylic acid and polyamine. However, he states that the molar ratio of the polyoxypropylene diamine or triamine to the dicarboxylic acid may range from about 0.25:1 to about 4.0:1. The thermoplastic adhesives of Klein are made by reacting the polyoxypropylene diamine or triamine with the dicarboxylic acid at about 175° to about 275° C. for about 1 to 12 hours.

The preparation of thermoplastic adhesives is disclosed in Schulze U.S. Pat. No. 4,119,615. The adhesives are prepared by a two-step process. In the first step, about 1 to 4 moles of oxalic acid esters is reacted with a polyoxyalkylene diamine or triamine, the preferred ratio being a mole ratio of about 1 to 2 moles of oxalic acid per mole of polyoxyalkylene diamine or triamine. This results in the formation of a so-called liquid prepolymer which is then reacted with an alkylene diamine such as ethylene diamine which contain 2 to 18 carbon atoms to provide the resinous polyoxyamide thermoplastic adhesive composition.

Mains et al. U.S. Pat. No. 4,062,819 is directed to polyamide polyblends wherein one component is a high molecular weight thermoplastic polyamide and the other is a minor amount of a polyamide derived from a high molecular weight dibasic acid. The second component is prepared by reacting a dicarboxylic acid such as "dimer acids" with an aliphatic alkylene diamine such as ethylene diamine.

Rieder U.S. Pat. No. 4,239,635 (reissued as U.S. Pat. No. Re. 30,885) is directed to lubricants modified by the inclusion of diamides. The diamides are carboxylic acid terminated reaction products of an excess of a dicarboxylic acid with a polyoxyalkylene diamine.

Rasmussen U.S. Pat. No. 4,218,351 discloses impact resistant thermoplastic polyamides which are suitable for use as hot melt adhesives and which contain, as a component, a minor amount of an amorphous amide-forming oligomer which is described as a polyoxyalkylene diamine having a number average molecular weight in the range of about 900 to about 5000.

Mitchell et al. U.S. Pat. No. 4,062,820 discloses copolyamides derived from a mixture of a polymeric fatty acid and a short chain dibasic acid with a mixture of amines composed of a polyoxyalkylene diamine and a short chain diamine such as ethylenediamine.

Rieder U.S. Pat. No. 4,239,635 is directed to aqueous metal working fluids containing a carboxylic acid group terminated polyoxyalkylene diamine or the alkali metal, ammonium or organic amine salts of the diamides. The diamide is prepared by reacting a dicarboxylic acid with a polyoxyalkylenediamine in a 2:1 mole ratio.

Chang U.S. Pat. No. 4,588,783 relates to heat curable compositions containing polyhydroxyethyl carbonates which are prepared by reacting an amidoamine with an organic carbonate. The amidoamines are prepared by reacting a polyester with an equivalent excess of a polyamine, for example, by reacting two moles of isophorone diamine with one mole of dimethylcyclohexane dicarboxylate.

Bently U.S. Pat. No. 4,751,255 is directed to polymeric polyamines prepared by reacting a polycarboxylic acid or an ester thereof with a stoichiometric excess of a polyamine having terminal aminopropoxy groups to provide polymeric polyamines containing 2 to 4 primary amine groups per molecule.

BACKGROUND OF THE PRESENT INVENTION

The polyoxyalkylene polyamines of the type disclosed in Yeakey U.S. Pat. No. 3,654,370 are prepared from polyoxyalkylene diols made by the oxyalkylation of a polyhydric alcohol, such as a glycol. The preferred starting materials are ethylene glycol or propylene glycol and propylene oxide or ethylene oxide. Copolymer polyols of ethylene oxide and propylene oxide are also useful.

The molecular weight of the polyol is determined by the number of moles of epoxide that are reacted with the alcohol initiator. Since the addition is random, the final alkoxylation product will not be a pure compound but, rather, will be a mixture of polyoxyalkylene polyols. For example, if the polyol is a polyol prepared by reacting propylene glycol with propylene oxide, using an amount of propylene oxide adequate to provide for an average molecular weight of about 1,000, the final propoxylation product will actually be composed of a mixture of polyoxypropylene diols having molecular weights varying from about 800 to about 1,200, the molecular weight distribution following a Gaussian distribution curve (sometimes referred to as a sine curve or a Poissan curve). As the molecular weight of the polyol increases, the spread in the molecular weights will also increase. Thus, when the average molecular weight of the diol is about 3,000, the deviation will be about ±400 molecular weight units so that most of the product will fall within the molecular weight range of about 2,600 to about 3,400.

As the molecular weight is still further increased, the percentage of free hydroxyl groups in the reaction mixture will decrease because of the added bulk of the already formed polyol, thus making the addition of more propylene oxide groups progressively more difficult. As a practical matter, when the diol reaches an average molecular weight of about 5,000, further propoxylation is accomplished only with extreme difficulty. The 5,000 molecular weight polyoxypropylene diols will have a molecular weight distribution of about ±1,000 so that the actual molecular weight range will be from about 4,000 to about 6,000. Again, the molecular weight distribution following a Gaussian distribution curve.

A further complication is encountered during the propoxylation to the higher molecular weights. As the reaction time and temperature are increased to encourage propoxylation, there is introduced a tendency on the part of the propylene oxide to isomerize to allyl alcohol and a tendency on the part of the hydroxypropyl end groups of the polyoxypropylene diol to dehydrate to form terminal olefin groups and water. Both the water and the allyl alcohol are susceptible to oxyalkylation thereby diluting the polyoxypropylene diol with undesired generally low molecular weight diol contaminants derived from the water and monofunctional allyl alcohol propoxylates. From as little as one percent to as much as ten percent of the oxypropyl end groups of the triol may dehydrate to form groups with terminal unsaturation in increasing the average molecular weight from about 3,000 to about 5,000.

When a polyoxypropylene polyol of this nature is reductively aminated in accordance with the procedure of Yeakey U.S. Pat. No. 3,654,370, comparatively higher temperatures and longer reaction times are required as the molecular weight of the polyol increases. This can result in the cleavage of the polyol to form undesired and unwanted alkyl ether by-products and hydrogenation of the unsaturated groups on the polyol to form propyl ethers.

Thus, although the results obtained heretofore with polyoxyalkylene diamines of the type disclosed by Yeakey have been generally satisfactory, problems such as those mentioned above have detracted from the utility of the products.

SUMMARY OF THE INVENTION

In accordance with the present invention, molecular weight distribution and terminal unsaturation problems such as those mentioned above are significantly reduced through the provision of the block amido-amine condensation products of the present invention which contains terminal primary amine groups analogous in function and reactivity to the primary amine groups of the polyoxyalkylene polyamines of Yeakey et al. but which are characterized by a significantly narrower molecular weight distribution and by significantly lower by-product contamination.

Another significant property of the block amido-amine condensation products of the present invention, as compared with the corresponding polyoxyalkylenepolyamines, is the desirable increase in the "stiffness" or "hardness" that is obtained without otherwise adversely affecting the other properties of the amido-triamine. For example, when the higher molecular weight polyoxyalkylene polyamines are used to cure epoxy resins, the resultant cured epoxy resin will frequently exhibit undesirable flex and hardness properties and other related characteristics attributable to the "rubbery" nature of the high molecular weight polyoxyalkylene polyamines. Thus, it is frequently necessary to use additives and/or fillers to provide a final cured epoxy resin having the desired physical properties. The block amidoamine condensation products of the present invention are significantly stiffer and can be used successfully with lesser quantities of fillers and/or additives or even without such additives.

The improvements of the present invention are obtained by reacting piperazine with two moles, per mole of piperazine, of the unsaturated acid component, as hereinafter defined. The reaction between the piperazine and the unsaturated acid component proceeds by the well-known Michael reaction to provide an intermediate reaction product, i.e.:

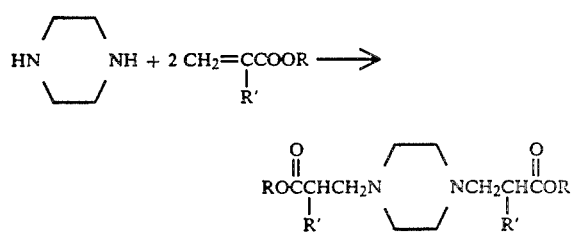

wherein

R represents hydrogen, a $C_1$–$C_8$ alkyl group, a hydroxyethyl group or a hydroxypropyl group, and R' represents hydrogen or methyl.

The unsaturated acid component to be used in accordance with the present invention is selected from the group consisting of acrylic acid, methacrylic acid, $C_1$–$C_8$ alkyl esters thereof, such as methyl acrylate, ethyl acrylate, propyl acrylate, isopropyl acrylate, butyl acrylate, amyl acrylate, octyl acrylate, etc., methyl methacrylate, ethyl methacrylate, propyl methacrylate, isopropyl methacrylate, butyl methacrylate, amyl methacrylate, octyl methacrylate, etc., hydroxyethyl or hydroxypropyl acrylate or hydroxyethyl or hydroxypropyl methacrylate.

The reaction between the piperazine and the unsaturated acid component is preferably conducted in a reactor provided with suitable agitation means at a temperature of about 30° to about 150° C. and a pressure of about 0 to 500 psig, and more preferably, at atmospheric pressure. The reaction can be conducted at higher or lower pressures, but there is no particular advantage in doing so. The reaction time required for completion of the reaction will normally range from about 0.5 to about 12 hours.

In accordance with the present invention, the intermediate reaction product is reacted with 2 moles of the diprimary amine component to provide the block amido-amine condensation products of the present invention, i.e.:

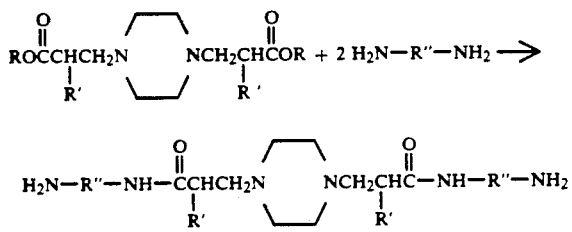

wherein

R represents hydrogen or a $C_1$–$C_8$ alkyl group or hydroxyethyl or hydroxypropyl groups, R' represents hydrogen or methyl, and R" represents an oxyalkylene group selected from the group consisting of polyoxyethylene groups, polyoxypropylene groups, and polyoxyethylene/oxypropylene groups, and polyethyleneamino groups, the polyoxyethylene groups having the formula:

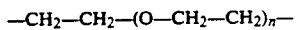

wherein n is a positive number having an average value of 1 to about 4.

The polyoxypropylene groups having the formula:

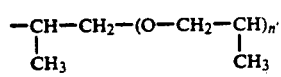

wherein n' is a positive integer having an average value of about 2 to about 100, the polyoxyethylene/oxypropylene groups having the formula:

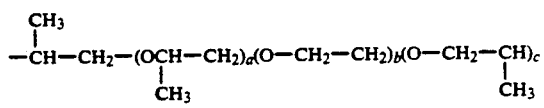

wherein a+c equals a positive number having a value of 2 to about 10 and b is a positive number having a value of from 1 to about 50, the polyethylene amino groups having the formula:

wherein n" is a positive integer having an average value of about 1 to about 5.

The Primary Diamine Starting Materials

The primary diamine starting materials for the present invention are selected from the group consisting of polyoxypropylenediamines, polyoxyethylenediamines, polyoxyethylene/oxypropylenediamines and polyethylenepolyamines.

Suitable polyoxypropylene diamines are sold by the Texaco Chemical Company as Jeffamine ® products having the formula:

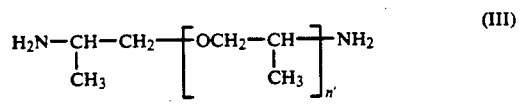

wherein n' is a positive number having an average value of about 2 to about 100.

Representative products having this structural formula include polyoxypropylene diols having an average molecular weight of about 230 wherein the value of n' is 2.6 (Jeffamine ® D-230 amine), polyoxypropylene diols having an average molecular weight of about 400 wherein n' has a value of 5.6 (Jeffamine ® D-400 amine), and a polyoxypropylene diol product having an average molecular weight of about 2,000 wherein n' has a value of about 33 (Jeffamine ® D-2000 amine) and a product having an average molecular weight of about 4,000 wherein n' has a value of about 60 (Jeffamine ® D-4005 amine).

Another appropriate class of polyoxyalkylene diamines, containing both ethylene oxide and propylene oxide, which may be used are polyoxypropylene diamines that are sold by the Texaco Chemical Company as Jeffamine ® ED-series products having the formula:

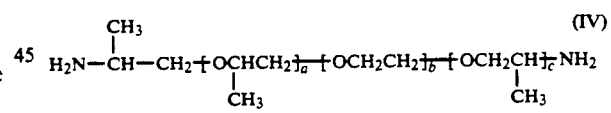

wherein a+c equals a number having a value of from about 2 to about 10 and b is a number having a value of from about 1 to about 50.

Examples of products having this general formula include a commercial product having an average molecular weight of about 600 where the value of b is about 13.5 and the value of a+c is about 3.5 (Jeffamine ® ED-600 amine), a commercial product having an average molecular weight of about 900 wherein the value of a+c is again about 3.5, but the value of b is about 20.5 (Jeffamine ® ED-900 amine). Other examples are those wherein a+c has a value of about 3.5 including a product having an average molecular weight of about 2,000 wherein the value of b is about 45.5 (Jeffamine ® ED-2001 amine) and a product having an average molecular weight of about 4,000 wherein the value of b is about 85 (Jeffamine ® ED-4000 amine).

Another group of diamines that may be used are the polyoxyethylenediamines having the formula:

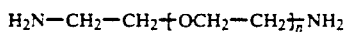

wherein n is a positive integer having a value of 1 to 4.

An example of such a product is bis-aminoethyl ether (BAEE) where n has a value of 1, a product sold by Texaco Chemical Company under the name Jeffamine® EDR-148 where n has a value of 2 and a product of Texaco Chemical Company under the name Jeffamine® EDR-192 where n has a value of 3.

Still another group of primary diamines that can be used as starting materials are polyethylenepolyamines having the formula:

wherein n" is a positive integer having an average value of about 1 to about 5.

Representative polyethylenepolyamines from this group include compounds such as diethylenetriamine, triethylenetetramine, tetraethylenepentamine and pentaethylhexamine.

Reaction Conditions

The reaction between the piperazine and the unsaturated component and the reaction between the intermediate condensation product are suitably conducted at a temperature of about 30° to about 250° C. and a pressure of about 0 to 500 psig. A catalyst is not required. Higher or lower pressures can be used, if desired, but there is no particular advantage is so doing.

The condensation products are normally liquid, although some of the products are solid at room temperature. The block amido-amine condensation products of the present invention have molecular weights within the range of about 300 to about 5000.

EXAMPLES

Table I summarizes a variety of amido-amines that can be made from our invention. It should be noted that water soluble amines can be made from.

1. Polyoxypropylene/polyoxyethylene diamines such as those of the D-series JEFFAMINE amines. The same is true from those products derived from the EDR-series amines and the lower molecular weight D-series amines. The new amines with water soluble properties are suitable for water borne coating or other applications which require avoiding organic solvents.

2. The products are liquid except those from the low molecular weight EDRseries. It is easier to handle liquid products in applications such as epoxy or reaction injection molding operations.

3. A secondary amine generally reacts slowly in the Michael reaction. However, piperazine reacts vigorously and is important in our scheme of reaction.

EXAMPLE 1

(6340-67): Adduct of piperazine, ethyl acrylate and JEFFAMINE EDR-192 (at 1:2:2 molar ratio)

To a 500 ml 3-necked flask equipped with a thermometer, a Dean-Stark trap, a stirrer and nitrogen-inlet line was charged ethyl acrylate (100 g, 1.0M). With stirring, piperazine (43 g, 0.5M) was added portionwise. An exothermic temperature at 33° C. was recorded. The mixture was then heated to 70° C. and held for over 1 hour. After cooling, a crystalline product was obtained. A portion of the above product (64 g, ca. 0.263M) was charged into the original apparatus and JEFFAMINE EDR-192 (111 g, 0.58M) was added. The mixture was heated to 130°-150° C. for 4 hours and 182° C. for 2 hours (under $N_2$-flow). An overhead light material ca. 13 ml was removed. The resulting product was a yellow liquid, with analyses of 7.0 meq/g total amine )6.9 g meq/g calc.) and viscosity at 453 cs/37.8° C.

EXAMPLE 2

Adduct of piperazine and ethyl acrylate (1:2) (6340-73)

To a 500 ml 3-necked flask equipped with a thermometer, a Dean-Stark trap, a stirrer and nitrogen inlet line was charged with ethyl acrylate (200 g, 2.0M). Then piperazine was added portionwise over ca. 1 hour period of time. An exothermic temperature at 43° C. was recorded. The mixture was heated at 50° C. for ca. 4 hours to give 283 g light colored solid. The H-nmr indicated the structure of (A).

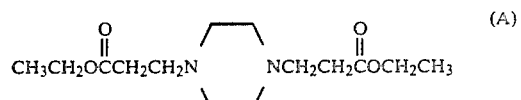

EXAMPLE 3

Adduct of DETA to piperazine-acrylate intermediate (6360-6)

To a 250-ml 3-necked flask equipped with a thermometer, a Dean-Stark trap, a stirrer and nitrogen-line was charged with product (6340-73) (85.8 g, 0.3M) and DETA (63.6 g, 0.6M). The mixture was heated to 170° C. for over 4 hours to remove ethanol. The resulting product was liquid with analyses of 14.7 meq/g total amine (calc. 14.9) and viscosity at 15,000 cs/25° C.

EXAMPLE 4

Usage Example (6360-6A)

A portion of product 6360-6 (18.5 g) was mixed with Epon 828 (Shell product, 51.3 g) and poured into a double panel mold container and cured at 150° C. for over 2 hours to give a brown hard solid material.

TABLE I

POLYAMINES CONTAINING ACTIVE AMINE AND PIEPRAZINE FUNCTIONALITY

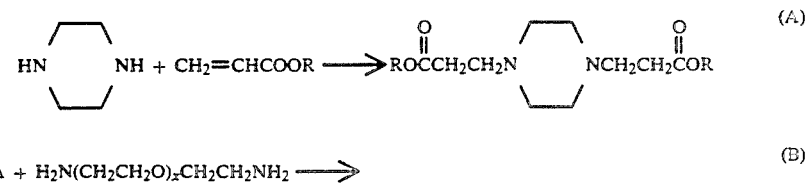

TABLE I-continued
POLYAMINES CONTAINING ACTIVE AMINE AND PIEPRAZINE FUNCTIONALITY

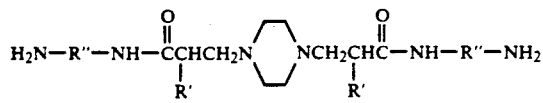

| Notebook No. | Amine | Amine Content (theoretical) (meq/g) | | Viscosity | Descriptions |
|---|---|---|---|---|---|
| 6360-6 | DETA | 14.7 | (14.9) | 15,000 cs/25° C. | Brown liquid |
| 6340-98 | EDR-148 | 7.8 | (8.2) | — | Water soluble Solid |
| 6360-46 | EDR-192 | 6.4 | (6.9) | 1800 cs/28° C. | Water soluble Yellow liquid |
| 6340-67 (repeat) | EDR-192 | 7.0 | (6.9) | 450 cs/37.8° C. | Yellow liquid |
| 6360-45 | D-230 | 6.8 | (6.1) | 105 cs/25° C. | Water soluble Yellow liquid |
| 6360-47 | D-400 | 4.6 | (4.0) | 90 cs/25° C. | Water soluble Yellow liquid Water soluble |

The foregoing examples have been given by way of illustration and are not intended as limitations on the scope of this invention, which is defined by the appended claims.

We claim:

1. A block amido-amine condensation product having the formula:

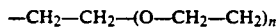

wherein
R' represents hydrogen or methyl, and
R" represents a polyoxyalkylene group selected from the group consisting of polyoxyethylene groups, polyoxypropylene groups, polyoxyethylene/oxypropylene groups, and polyethyleneamino groups,
said polyoxyethylene groups having the formula:

$$-CH_2-CH_2-(O-CH_2-CH_2)_n$$

wherein n is a positive number having an average value of 1 to about 4,
said polyoxypropylene groups having the formula:

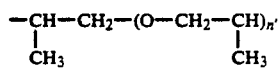

wherein
n' is a positive integer having an average value of about 2 to about 100,
said polyoxyethylene/oxypropylene groups having the formula:

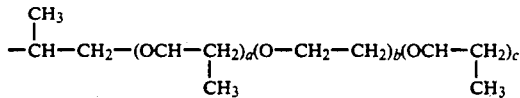

wherein
a+c equals a positive number having a value of 2 to about 10 and b is a positive number having a value of from 1 to about 50, and
said polyethylene amino groups having the formula:

wherein
n" is a positive integer having an average value of about 1 to about 5.

2. A block amido-amine condensation product as in claim 1 wherein R' represents hydrogen and wherein R" is a polyoxyethylene group.

3. A block amido-amine condensation product as in claim 2 wherein the value of n in the polyoxyethylene diamino group is 2 or 3.

4. A block amido-amine condensation product as in claim 1 wherein R' represents hydrogen and wherein R" is a polyoxypropylene group.

5. A block amido-amine condensation product as in claim 4 wherein the value of n' in the polyoxypropylene diamino group is about 2.6 or about 5.6.

6. A block amido-amine condensation product as in claim 1 wherein R' represents hydrogen and wherein the diprimary amine group is a polyethylene amino group.

7. A block amido-amine condensation product as in claim 6 wherein the value of n' in the polyethylene amino group is 1.

* * * * *